United States Patent [19]
Sanaka

[11] Patent Number: 6,153,581
[45] Date of Patent: *Nov. 28, 2000

[54] DRUG FOR RECOVERING RENAL FUNCTION

[75] Inventor: Tsutomu Sanaka, Tokyo, Japan

[73] Assignee: Sumitomo Pharmaceuticals Company, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/043,823

[22] PCT Filed: May 9, 1996

[86] PCT No.: PCT/JP96/01225

§ 371 Date: Mar. 27, 1998

§ 102(e) Date: Mar. 27, 1998

[87] PCT Pub. No.: WO97/12631

PCT Pub. Date: Apr. 10, 1997

[30] Foreign Application Priority Data

Sep. 29, 1995 [JP] Japan ..................................... 7-276467

[51] Int. Cl.$^7$ ............................. A61K 38/27; C07K 14/61
[52] U.S. Cl. .............................. 514/12; 530/399; 930/120
[58] Field of Search .............................. 530/399; 514/12; 930/120

[56] References Cited

PUBLICATIONS

Sanaka, Tsutomu. "Long–Term Effect of Recombinant Human Growth Hormone (rhGH) on progression of End–Stage Renal Disease (ESRD)" Journal of the American Society of Nephrology; Sep. 1995, vol. 6, No. 3, p. 1030.

Ziegler, Thomas R. "Effects of Recombinant Human Growth Hormone in Adults Receiving Maintenance Hemodialysis." Journal of the American Society of Nephrology; 1991, vol. 2, No. 6, pp. 1130–1135.

Kopple, Joel D. "Growth hormone treatment for patients with renal failure." Japanese Journal of Nephrology; 1991, vol. 33, No. 5, pp. 468–474.

Andersson, Hans C. "Effect of growth hormone treatment on serum creatinine concentration in patients with cystinosis and chronic renal disease." The Journal of Pediatrics; May 1992, vol. 120, No. 5, vol. 6, No. 5, pp. 716–720.

Mehls et al. Acta Paediatr. Suppl. 399:81–87, 1994.

Guyton. Textbook of Medical Physiology, 8th ed. WB Sauders Co, pp. 344–348, 1991.

*Primary Examiner*—John Ulm
*Assistant Examiner*—Christine Saoud
*Attorney, Agent, or Firm*—Birch, Stewart, Kolasch Birch, LLP

[57] ABSTRACT

Drug which contains human growth hormones capable of recovering the renal function when administered to a patient who has renal insufficiency but has not yet undergone kidney dialysis. By administrating the drug, the loss of renal function represented by an extreme decrease in creatinine clearance or the reciprocal of blood creatinine level can be prevented and thus it can dispense with the dialytic treatment for patients with renal insufficiency.

7 Claims, 3 Drawing Sheets

DRUG FOR RECOVERING RENAL FUNCTION

This application is the national phase under 35 U.S.C. §371 of prior PCT International Application No. PCT/JP96/01225 which has an International filing date of May 9, 1996 which designated the United States of America.

FIELD OF THE INVENTION

The present invention relates to a drug for recovering renal function. In particular, the present invention relates to a drug for treating progressive renal dysfunction in a patient with renal failure who has not yet undergone kidney dialysis.

BACKGROUND OF THE INVENTION

Presently, human growth hormone (referred to hereinafter as hGH) is used to treat pituitary dwarfism. In addition, it is also reported to be useful in acceleration of healing of bone fracture and burn wound, as well as in the treatment of patients of malnutrition (94/95 Nikkei Baio Nenkan). According to the following papers, hGH has been examined for its improving effect on the growth failure of short children having renal failure and also administrated to adult patients having renal failure. However, the papers only demonstrate the ameliorating effect of hGH on the malnourished conditions of patients who are undergoing dialysis, i.e., who have lost their renal functions.

1. KOPPLE, J. D. et al., *Nippon Jinzo Gakkai-shi* 33:468–474 (1991): "Growth hormone treatment for patients with renal failure".
2. Sanaka, Sugino et al., *Nippon Jinzo Gakkai-shi* 33:1153–1159 (1991): "Improvement of malnutrition indices in adult patients with end stage renal disease by rhGH".

It has not been reported in the above papers that hGH may be useful for recovering progressive renal dysfunction in a patient with renal failure who has not yet undergone dialysis.

To date, there is not available a drug effective in maintaining or restoring the renal function of patients with end stage renal failure who have not yet undergone dialysis. Thus there is no way to prolong their lives except for such a treatment as renal dialysis or renal transplantation which is highly risky and burdensome to the patients.

SUMMARY OF INVENTION

The object of the present invention is to provide a drug for treating progressive renal dysfunction in a patient with renal failure who has not yet undergone dialysis. Such a drug allows patients to avoid or delay the start of kidney dialysis for patients with end stage renal failure. The method of the present invention may protect them from irreversible loss of renal function.

DETAILED DESCRIPTION OF THE PRESENT INVENTION

Figure 1:
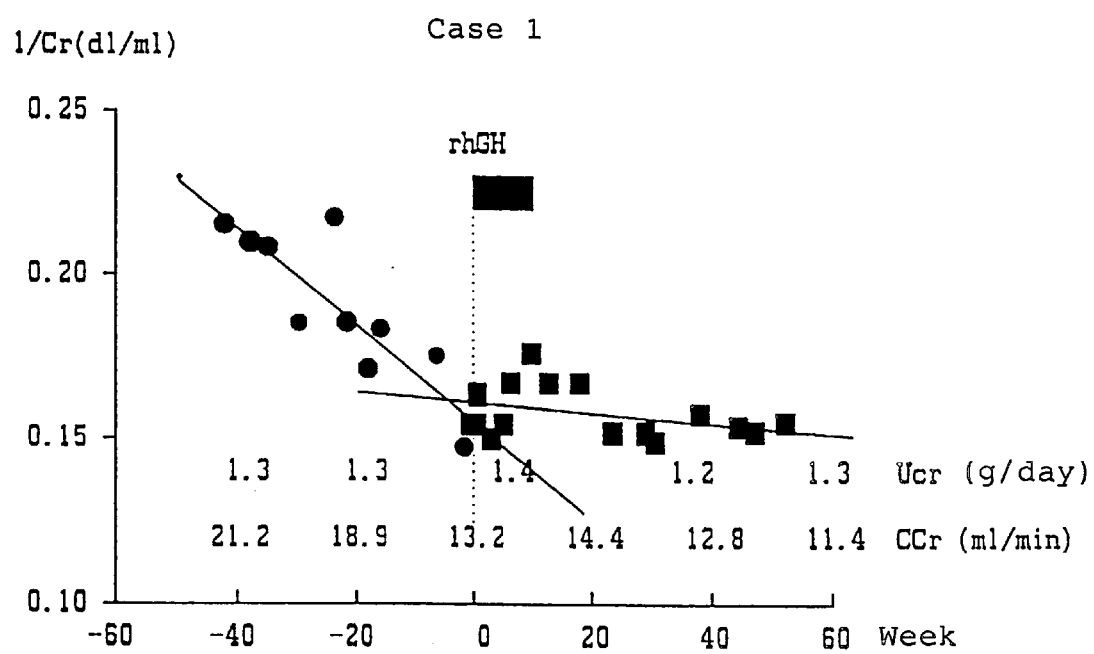
FIG. 1 shows observations during 60 weeks before and after hgH administration in Case 1 of Example 1. The line graph and the ordinate show the 1/Cr value (reciprocal of the serum creatinine concentration), and the numerals at the lower part of the graph show the CCR value (creatinine clearance) and the Ucr value (the amount of secreted creatinine in urine).

The present inventors have hitherto used hGH to ameliorate the nourishment of renal failure patients who undergo dialysis. Surprisingly, the inventors have now found that, when administered to renal failure patients who have not undergone dialysis, hGH can improve their renal function which had been steadily deteriorating until then, and can avoid the start of hemodialysis therapy (which starts based on blood 1/Cr value<0.1 dl/mg). The present invention has been accomplished on the basis of this finding.

Thus, the present invention relates to a drug for treating progressive renal dysfunction in a renal failure patient who has not yet undergone dialysis, which comprises hGH as an active ingredient. In addition, the present invention relates to a method for treating renal dysfunction in a renal failure patient who has not yet undergone dialysis, which comprises administrating an effective amount of hGH to said patient.

The present invention will be described below in detail.

Presently, hGH is used for treatment of pituitary dwarfism, and various preparations containing a recombinant hGH such as Genotropin are commercially available. For the purpose of the present invention, any variant that has the hGH activity may be used, although mature hGH is more preferable in terms of, for example, antigenicity. For example, native preparation purified from the pituitary gland, Met-hGH in which a methionine residue is attached to the N-terminus of native hGH, or even recombinant hGH variants may be used as long as they have hGH activity. Therefore, the term "human growth hormone (hGH)" as used herein encompasses all hGH derivatives having hGH activity regardless of their origins or producing process.

As used herein, the term "hGH activity" means the general growth-promoting activity which, as conventionally known, grows every human tissue (especially bone), primarily in the process of growing, with the exception of the brain. All or parts of known physiological properties of hGH, such as promotion of bone/cartilage proliferation via somatomedin (IGF-I) induction, promotion of amino acid uptake by cell and protein synthesis or inhibition of protein degradation, promotion of neutral lipid metabolism, promotion of saccharide metabolism, or promotion of electrolyte preservation, are included in the hGH activity.

A pharmaceutical formulation, in the form of a solution or lyophilization, may be used. In any case, formulations suitable for subcutaneous administration are especially preferred. In these parenteral formulations, stabilizers and carriers known in the art may be used, and such formulations are preferably used in the form of isotonic solutions when used. As a pharmaceutically acceptable carrier, plasma-derived proteins such as albumin, amino acids such as glycine, and saccharides such as mannitol may be used. Suitable examples of carriers are described in the Japanese Patent Publication (KOHYOU) H3-503764.

The term "patients with renal failure who have not yet undergone dialysis" as used herein means patients with renal failure due to proliferative glomerulonephritis, mesangial proliferative glomerulonephritis, membranaceous nephropathy, chronic nephritis (nephropathy) or glomerulosclerosis such as diabetic nephropathy, nephrosis syndrome, kidney ischemia or the like, who have not undergone dialysis therapy, and primarily refers to those patients having a degree of progressive renal dysfunction in the range of 0.1 dl/mg to 0.5 dl/mg when represented by a 1/Cr value (reciprocal of serum creatinine value, one of indexes of renal function), or in the range of 5 ml/min to 50 ml/min when represented by a CCr value (creatinine clearance value, one of indexes of renal function). Particularly suitable subjects are those patients with end stage renal failure who exhibit a 1/Cr value in the range of 0.1 dl/mg to 0.3 dl/mg, or a CCr value in the range of 6 ml/min to 15 ml/min.

The condition described above is just one step before the requirement of kidney dialysis therapy. Although the renal function is still maintained, such condition will lead to loss of renal function when left untreated. The patients may receive a dietary cure usually used for the patients in this phase, and combination of such dietary cure and hGH administration according to the present invention is expected to have an advantageous effect. Namely, hGH acts on the kidney and remarkably improves or maintains the impaired renal function.

The mode of hGH administration may be subcutaneous, intravenous, or intramuscular. Subcutaneous administration is usually employed.

Although the dosage of hGH should be varied appropriately depending on, for example, the condition, age and sex of a particular patient, it is usually preferred to administer intermittently 5–50 IU/week/patient for maximal 3 months, and particularly 10–30 IU/week/patient for more than one week up to 2 months.

As described above, the hGH-containing formulation of the present invention has an effect of remarkably improving or maintaining the renal function of a patient with renal failure who has not yet undergone dialysis, and provides a means for avoiding entering into the dialysis therapy which has been hitherto inevitable for the patients with renal failure who have not undergone dialysis.

EXAMPLES

The present invention will be described by making reference to the following examples.

Example 1

Case 1: a male patient aged 38 who has fallen into chronic renal failure due to mesangium proliferative nephritis, which is complicated with hypertension. At the start of the hGH administration, he was 170 cm height, 58 kg weight, with a CCr value of 13.2 ml/min, and under a dietary cure of 2200 kcal and 40 g protein. Two courses of hGH administration (subcutaneous) were given over 1.5 months providing that one course consists of 4 units/day×7 days.

As a result of the hGH administration, the decrease in 1/Cr value was stopped as shown in FIG. 1, and the 1/Cr value was maintained at the level of 0.15. In addition, the decreasing rate of CCr value also slowed down from 8 ml/min/40 weeks before the administration (from 21.2 ml/min to 13.2 ml/min) to 1.8 ml/min/40 weeks (from 13.2 ml/min to 11.4 ml/min) after the administration. As a result, the necessity of kidney dialysis for this patient was circumvented, and such condition has been still maintained until now (60 weeks after the initiation of hGH administration).

In general, there are two conceivable causes for repression of increase in serum creatinine value: (1) an elevation of the creatinine excretion ability due to the improvement of renal function, and (2) decrease in creatinine production due to decrease in the amount of muscle. In this case, however, the repression of increase in serum creatinine value was considered due to the improvement of renal function, since the amount of excreted creatinine in urine was not changed during the procedure.

Example 2

Case 2: a female patient aged 45 who has fallen into chronic renal failure from gestosis, which is complicated with hypertension. At the start of the hGH administration, she was 145 cm height, 54 kg weight, with a CCr value of 13.0 ml/min, and under a dietary cure of 1800 kcal and 25 g protein. The hGH administration (subcutaneous) with the dosage of 12 IU/week/patient was applied for 2 months.

Figure 2:
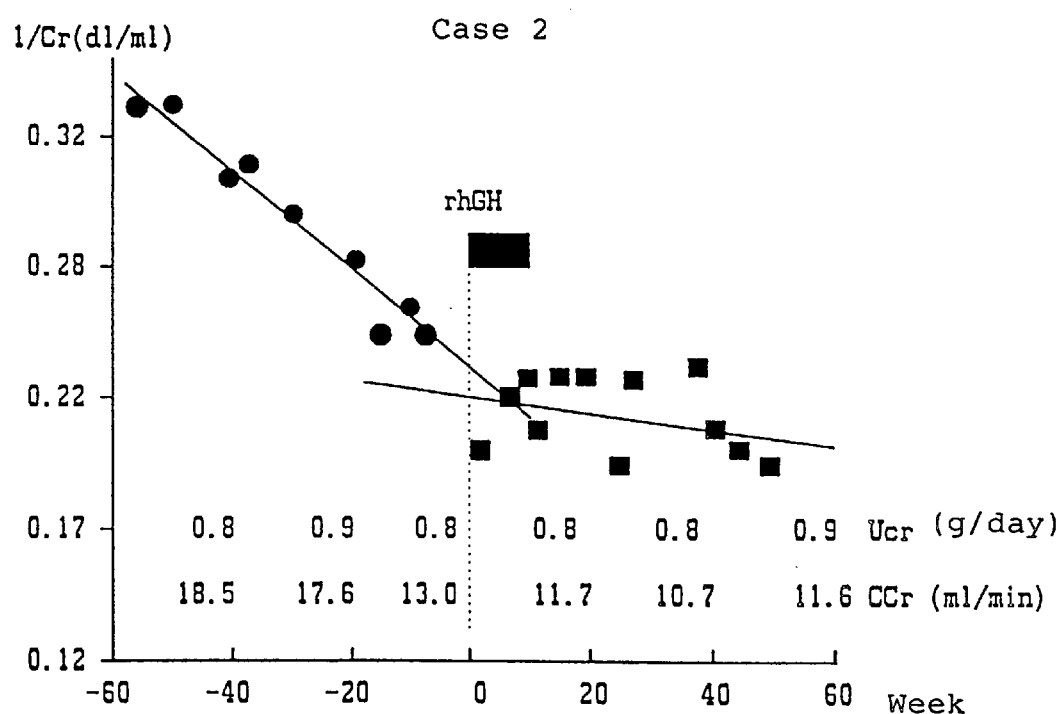
FIG. 2. shows observations during 60 weeks before and after the hgH administration in Case 2 of Example 2. The line graph and the ordinate show the 1/Cr value (reciprocal of the serum creatinine concentration), and the numerals at the lower part of the graph show the CCr value (creatinine clearance) and the Ucr value (the amount of secreted creatinine in urine).

As a result of the hGH administration, the decrease in 1/Cr value was stopped as shown in FIG. 2, and the 1/Cr value was maintained at the level of 0.17. In addition, the decreasing rate of CCr value also slowed down from 5.5 ml/min/40 weeks (from 18.5 ml/min to 13.0 ml/min) before the administration to 1.4 ml/min/40 weeks (from 13.0 ml/min to 11.6 ml/min) after the administration. As a result, the necessity of kidney dialysis for this patient was circumvented, and such condition has been still maintained until now (60 weeks after the initiation of hGH administration). The repression of increase in serum creatinine value was not considered due to decrease in the amount of muscle, since the amount of excreted creatinine in urine was not changed during the procedure.

Example 3

Case 3: a female patient aged 44 who has fallen into chronic renal failure from chronic nephritis, which is complicated with hypertension. At the start of the hGH administration, she was 154 cm height, 57 kg weight, with a CCr value of 6.5 ml/min, and under a dietary cure of 1800 kcal and 25 g protein. The hGH administration (subcutaneous) with the dosage of 12 IU/week/patient was applied for 2 months.

Figure 3:
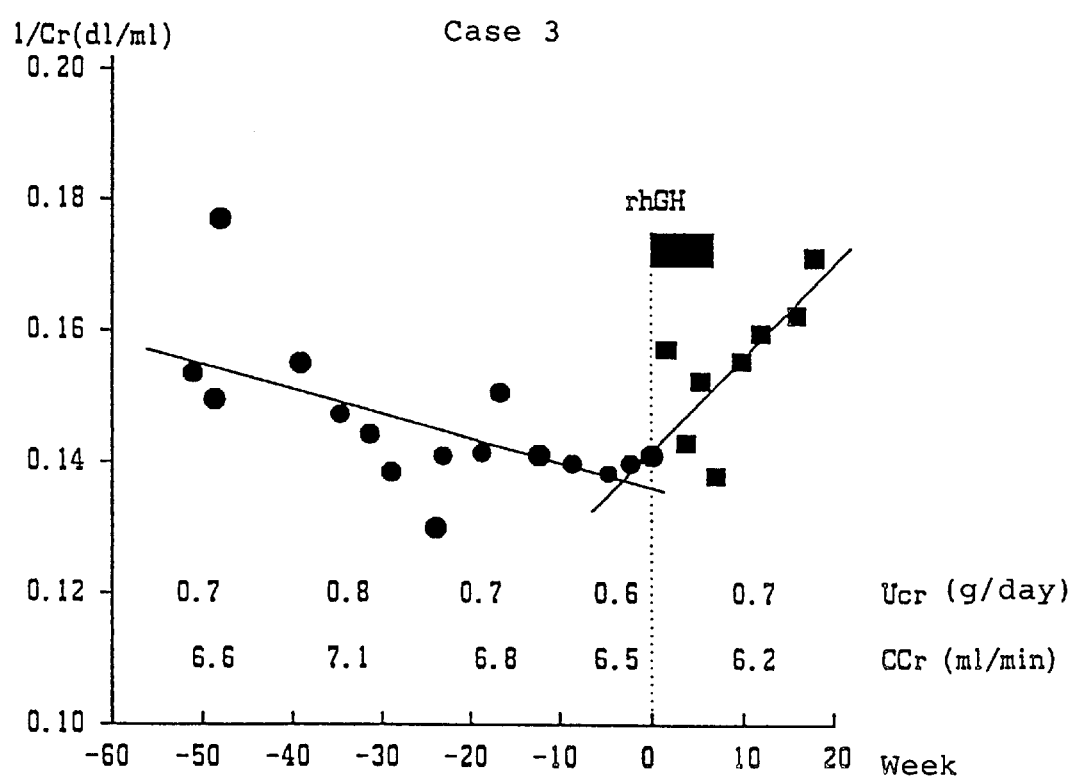
FIG. 3. shows observations during 60 weeks before and 20 weeks after the hgH administration in Case 3 of Example 3. The line graph and the ordinate show the 1/Cr value (reciprocal of the serum creatinine concentration), and the numerals at the lower part of the graph show the CCr value (creatinine clearance) and the Ucr value (the amount of secreted creatinine in urine).

As a result of the hGH administration, the decrease in 1/Cr value was stopped as shown in FIG. 3, and the 1/Cr value has changed from the level of 0.13 to 0.18 after 20 weeks of administration, exhibiting recovering trend. The CCr value was constantly about 6–7 ml/min over 50 weeks before the administration, and it was maintained at the same level also after the administration. As a result, the necessity of kidney dialysis for this patient was circumvented, and such condition has been still maintained until now (20 weeks after the initiation of hGH administration).

Formulations

The lyophilized formulation suitable for subcutaneous administration of hGH in the present invention may be prepared in the following manner.

One mg of purified recombinant hGH, 0.34 mg of glycine, 9 mg of mannitol, and 0.2 mg of a nonionic surfactant Polysorbate 80 are dissolved in one ml of phosphate buffer (pH 7.4, 5 mM). This solution is put into a vial and lyophilized to give a lyophilized formulation for subcutaneous administration.

The amount of glycine used as a stabilizer is preferably 50 to 200-fold relative to hGH (mole ratio). Preferably, 700 to 3000-fold of mannitol and 0.7 to 30-fold of Polysorbate 80 are used relative to hGH. Preferred pH of the buffer is 4–8.

The hGH-containing formulation of the present invention has an effect of remarkably recovering or maintaining the renal function of a patient with renal failure who has not yet undergone dialysis, and allows to the patients avoid the dialysis therapy which has been hitherto inevitable for patients with end stage renal failure.

I claim:

1. A method for treating progressive renal dysfunction in an adult patient with renal failure who has not yet undergone kidney dialysis and who does not exhibit growth hormone deficiency, which comprises administering an effective amount of human growth hormone to said patient to improve or maintain renal function, before undergoing kidney dialysis.

2. A method of claim 1, in which the human growth hormone is subcutaneously administered to said patient.

3. The method of claim 1, wherein a degree of progressive renal dysfunction in the patient with renal failure who has not yet undergone kidney dialysis is represented by a 1/Cr value in the range of 0.1 dl/mg to 0.5 dl/mg.

4. The method of claims 1, wherein the 1/Cr value is in the range of 0.1 dl/mg to 0.3 dl/mg.

5. The method of claim 1, wherein a degree of progressive renal dysfunction in the patient with renal failure who has not yet undergone kidney dialysis is represented by a CCr in the range of 5 ml/min to 50 ml/min.

6. The method of claim 1, wherein the CCR value is in the range of 6 ml/min to 15 ml/min.

7. The method of claim 1, wherein the human growth hormone is a recombinant human growth hormone.

* * * * *